US011761961B2

United States Patent
Wang et al.

(10) Patent No.: US 11,761,961 B2
(45) Date of Patent: Sep. 19, 2023

(54) BIOSENSING CHIP AND METHOD FOR DISTINGUISHING CANCER LESION SITE AND DEGREE OF CANCER LESIONS

(71) Applicant: NATIONAL CHUNG CHENG UNIVERSITY, Chia-Yi (TW)

(72) Inventors: Hsiang-Chen Wang, Chiayi (TW); Chun-Ping Jen, Tainan (TW); Hong-Wei Fan, Toufen (TW); Shin-Che Wang, Pingtung (TW)

(73) Assignee: NATIONAL CHUNG CHENG UNIVERSITY, Chia-Yi (TW)

( * ) Notice: Subject to any disclaimer, the term of this patent is extended or adjusted under 35 U.S.C. 154(b) by 442 days.

(21) Appl. No.: 16/933,125

(22) Filed: Jul. 20, 2020

(65) Prior Publication Data

US 2021/0318313 A1 Oct. 14, 2021

(30) Foreign Application Priority Data

Apr. 14, 2020 (TW) .................................. 109112515

(51) Int. Cl.
*B03C 5/00* (2006.01)
*G01N 27/26* (2006.01)
(Continued)

(52) U.S. Cl.
CPC .......... *G01N 33/574* (2013.01); *B03C 5/005* (2013.01); *B03C 5/026* (2013.01); *G01N 27/26* (2013.01);
(Continued)

(58) Field of Classification Search
CPC .... G01N 27/327–3272; G01N 27/3275–3278; G01N 27/305; B03C 5/005; B03C 5/026; B03C 5/028
See application file for complete search history.

(56) References Cited

U.S. PATENT DOCUMENTS 5,567,302 A * 10/1996 Song .................. G01N 27/3277
204/406
6,004,442 A * 12/1999 Choulga ............ G01N 27/3275
204/415
(Continued)

FOREIGN PATENT DOCUMENTS

CN 108362751 A * 8/2018 ........... G01N 27/327
TW 201945727 A 12/2019

OTHER PUBLICATIONS

TO-6 Package description by EESEMI Comprehensive reference on Semiconductor Manufacture, published 2008, downloaded https://eesemi.com/to5.htm on Mar. 21, 2023 (Year: 2008).*
(Continued)

*Primary Examiner* — Alexander S Noguerola
(74) *Attorney, Agent, or Firm* — Apex Juris, pllc; Hilde Coeckx

(57) ABSTRACT

A biosensing chip is provided, including a substrate having a photoelectric conversion material, and an electrode disposed on the substrate and including two contact portions and an electrode pattern, wherein the photoelectric conversion material is a monocrystalline silicon material, and the electrode pattern includes micro-electrodes in the form of interdigitated sawtooth. The biosensing chip and the method using the same may distinguish a lesion site of cancer cells and the degree of cancer lesions.

8 Claims, 8 Drawing Sheets

Before applying dielectrophoresis
(a) CE81T,6000 cell

After applying dielectrophoresis
(b) CE81T,6000 cell (a) CE81T,30000 cell (b) CE81T,30000 cell

(51) Int. Cl.
*G01N 33/574* (2006.01)
*G01N 33/543* (2006.01)
*B03C 5/02* (2006.01)

(52) U.S. Cl.
CPC . *G01N 33/5438* (2013.01); *G01N 2800/7028* (2013.01)

(56) References Cited

U.S. PATENT DOCUMENTS

| | | | |
|---|---|---|---|
| 10,294,099 B1* | 5/2019 | Biaggi-Labiosa ... | G01N 33/004 |
| 2004/0011650 A1 | 1/2004 | Zenhausern et al. | |
| 2008/0220535 A1* | 9/2008 | LeBoeuf ............. | G01N 27/414 436/164 |
| 2009/0211922 A1* | 8/2009 | Sasaki ................ | G01N 27/3271 205/782 |
| 2017/0326558 A1* | 11/2017 | Mahshid ................ | B03C 5/005 |

OTHER PUBLICATIONS

Merriam-Webster online dictionary definition of "radius", downloaded Mar. 21, 2023. (Year: 2023).*
David Leadley, "III-V Compound Semiconductors", University of Warwick Department of Physics online website https://warwick.ac.uk/fac/sci/physics/current/postgraduate/regs/mpagswarwick/ex5/intro/iii-v-compoundsemiconductors/ 2010, downloaded Mar. 22, 2023 (Year: 2010).*
EPO computer-generated English langauage translation of CN 108362751 A, downloaded Mar. 21, 2023, patent published Aug. 3, 2018 (Year: 2018).*
Patricia Shapley, "Commercial Solar Cells," University of Illinois 2012 online article downloaded Mar. 22, 2023 from http://butane.chem.uiuc.edu/pshapley/genchem2/c5/1.html (Year: 2012).*
Search report for TW109112515, dated Sep. 3, 2020, Total of 1 page.

\* cited by examiner

BIOSENSING CHIP AND METHOD FOR DISTINGUISHING CANCER LESION SITE AND DEGREE OF CANCER LESIONS

CROSS-REFERENCE TO RELATED APPLICATION

This application claims priority from Taiwan Patent Application No. 109112515, filed on Apr. 14, 2020, in the Taiwan Intellectual Property Office, the content of which is hereby incorporated by reference in its entirety for all purposes.

BACKGROUND

1. Technical Field

The present disclosure relates to a biosensing chip, particularly to a biosensing chip and methods capable of distinguishing a lesion site of cancer cells and a degree of lesions.

2. Description of the Related Art

Cancer is a disease due to an abnormal proliferation of tissue cells which causes the formation of a tumor. The cells may be transferred to other sites by a circulating system and further become circulating tumor cells. Before the onset of disease, these cells are unlikely to be detected from blood or in a living tissue sample, particularly metastatic tumor cells, which shows a very unique form of activity. From the past experiments, it is known that the cancer cells may mainly be divided into four pathological stages, from the initial superficial type to the final transfer type. As the cancer cells in a rather latter stage are transferred to other sites, the chances of receiving treatments may decrease. Corresponding methods and tools are required to quickly identify sites and morphology of cancer cells, wherein a biosensor is one of the common selections.

In the mid-20th century, after the concept of enzyme electrode was proposed, biosensors began to be developed for commercialization and mass production, which disclosed the initial generation of biosensor markets. In 1979, the biosensors began to be invested in the field of medical examination. The initial products were biosensors for blood glucose detection. Furthermore, mediator molecules were developed for the improvement of response time and sensitivity of a sensor, and the products have become mainstream commodities in the medical inspection market after pen-type and credit card-type portable small biosensors have been developed.

With the development of technology, the development of second-generation biosensors has been defined as the use of antibodies or receptor proteins as molecular recognition elements, the selection of signal converters has become more diverse. For instance, a field-effect transistor (FET), an optical fiber (FOS), a piezoelectric crystal (PZ), a surface acoustic wave device (SAW) may be used as a signal transducer.

The developing third-generation biosensors are positioned as sensors with more portable, automatic monitoring, and real-time monitoring functions, such as array biosensors developed with MEMS technology, which mostly are immunosensors. However, due to the variability of an enzyme, enzyme array biosensors are not suitable for being fixed to a substrate surface via covalent bonding or cross-linking technology, which indicates that there is still room for improvement.

Regarding the principle of dielectrophoresis (DEP), the polarization phenomenon occurs because of an electric field effect, and the dipole moment and electric field generated by polarization generate a dielectrophoretic force. Dielectrophoresis may be widely used to manipulate, separate, and aggregate cells, bacteria, biomolecules, nucleic acids in a non-destructive manner. When manipulating cells, no modification to other substances is required, which causes minimal damage to cells. Moreover, dielectrophoresis may be performed with the non-contact operation and manipulated in a single or a group, thus being suitable for cell manipulation. Dielectrophoresis is mainly based on different dielectric properties (degree of electric conduction and dielectric constant) between particles and solutions, and uses a non-uniform AC electric field to cause the particles to generate an asymmetric induced polarization ability to move particles toward a position with the high or low electric field intensity for separation after the electric field effect. In a case when particles in a solution are polarized by an electric field, if the polarizability of the particles is superior to that of the surrounding solution, the number of charges generated inside the particles may be higher than that of the surrounding solution, resulting in uneven distribution of charge density and making the direction of the electric dipole the same as that of the electric field. In contrast, if the polarizability of the particles is inferior to that of the surrounding solution, the number of charges in the surrounding solution may be higher than that on the particle surface, making the direction of the electric dipole to be opposite to that of the electric field. The phenomenon of dielectrophoresis depends on the polarizability of the particles and the medium solution, and the factors that determine the degree of the dielectrophoresis movement are electric conductivity and dielectric constant, wherein the higher the electric conductivity, the faster the charge movement, and the lower the electric conductivity, the slower the charge movement. Therefore, the ability to affect the storage and accumulation of charge in a particle is the dielectric coefficient.

In recent years, research on biomedical technology has gradually been emphasized, wherein lab-on-a-chip has gained great attention from many national research teams who successively made considerable effort to develop a chip equipped with the abilities to reduce sample consumption, degrease manpower requirements, accelerate inspection speed, simplify operation procedures, and save space of a laboratory. The chip with a few centimeters in size is a tiny device that may accomplish the analysis of samples conducted in the past with a wide range of applications. Specifically, DEP has attracted the most attention from research teams from various countries because it is often necessary to conduct research on specific samples in biomedical measurement analysis. For instance, on the continuous size separation, these samples may be bacteria, cells, etc. Different electrical polarization may occur on the particles through mainly using different dielectric properties between particles and solution with an uneven electric field, resulting in the particles respectively moving toward positions with different electric field intensities to generate displacements, thus achieving the effect of particle separation. The size and direction of the generated dielectrophoresis and the dielectric properties between the particles and the solution are interrelated with the intensity of a given external alternating electric field, particle size, the variation rate of the electric field, and frequency. When the polarizability of the particles is superior to that of the surrounding solution, the particles move in the direction of a high electric field gradient to form positive dielectrophoresis (pDEP). On the contrary, when the polarizability of the particles is inferior to the surrounding solution, the particles move in the direction of a low electric field gradient to form negative dielectrophoresis (nDEP).

Research on manufacturing micro-electrodes on silica through lithography technology has also been conducted with 5 μl of gold nanoparticles dropped on the electrode and alternating current applied with a probe. The variation in gold nanoparticles is observed at different electrodes and different voltages. When the voltage is 8V, the gold nanoparticles may form a regular string of pearls in just 1 second. Moreover, it is found that when the current passed is too high, high current may melt the gold nanoparticles in the electrode gap. This experiment has also realized the integration of dielectrophoresis in microelectrode arrays.

SUMMARY

To increase the recognition speed of cancer cells and save consumables, one objective of the present disclosure is to provide a biosensing chip that may be used to simultaneously detect cancer cell impedance and photocurrent effects.

Based on the above objective, the present disclosure provides a biosensing chip, including: a substrate including a photoelectric conversion material and an electrode disposed on the substrate and including two contact portions and an electrode pattern; the photoelectric conversion material is a monocrystalline silicon material, a metal oxide, an III-V compound semiconductor, or an II-VI compound semiconductor material.

Preferably, the electrode pattern includes a plurality of micro-electrodes spaced apart from each other.

Preferably, the plurality of micro-electrodes are interdigitated sawtooth electrodes in a shape of circular and straight lines with an electrode gap radius of about 30 μm to 80 μm.

Preferably, the plurality of micro-electrodes are spaced apart from each other by about 60 μm to 160 μm.

Preferably, the electrode is made of gold-chromium alloy, graphene, or graphene oxide.

Based on the above objective, the present disclosure further provides a method for distinguishing a lesion site of cancer cells, including the following steps: applying a cell suspension liquid comprising a test cell after being quantified to an electrode pattern of a biosensing chip; applying an electric signal to two contact portions of the biosensing chip by a signal generator; connecting a sensor to the two contact portions of the biosensing chip to measure an admittance value of the test cell.

Preferably, the electric signal is a voltage at 1 MHz and 10 Vp-p lasting for about 5 minutes.

Preferably, in a step of measuring the admittance value of the test cell, the sensor measures with a voltage at 500 kHz and 1 Vp-p.

Based on the above objective, the present disclosure further provides a method for distinguishing a degree of cancer lesions, including the following step: applying a cell suspension liquid after being quantified to an electrode pattern of a biosensing chip; connecting a sensor to the two contact portions of the biosensing chip to sense signals; waiting for a first predetermined time to stabilize the biosensing chip in a dark room; turning on a light for a second predetermined time, then turning off the light and lasting for a third predetermined time, and collecting values of a photocurrent response by the sensor.

Preferably, the first predetermined time is 30 seconds to 1 minute, the second predetermined time is 10 seconds to 30 seconds, and the third predetermined time is 10 seconds to 70 seconds.

With the above technical features, the biosensing chip and the method for distinguishing a lesion site of cancer cells and the degree of lesions provided by the present disclosure have the following advantages:

(1) The biosensor may be used for simple and fast detection.
(2) A single-chip biosensor may be used to simultaneously distinguish types of cancer cells and the degree of lesions and reduce costs.
(3) The micro-electrodes may be used to improve accuracy of detection.

BRIEF DESCRIPTION OF THE DRAWINGS

The accompanying drawings as follows are included to provide a further understanding of the present disclosure and incorporated to form a part of the specification. The drawings illustrate exemplary embodiments of the present disclosure together with the specification to explain the concept of the present disclosure.

DESCRIPTION OF THE PREFERRED EMBODIMENTS

Figure 1:
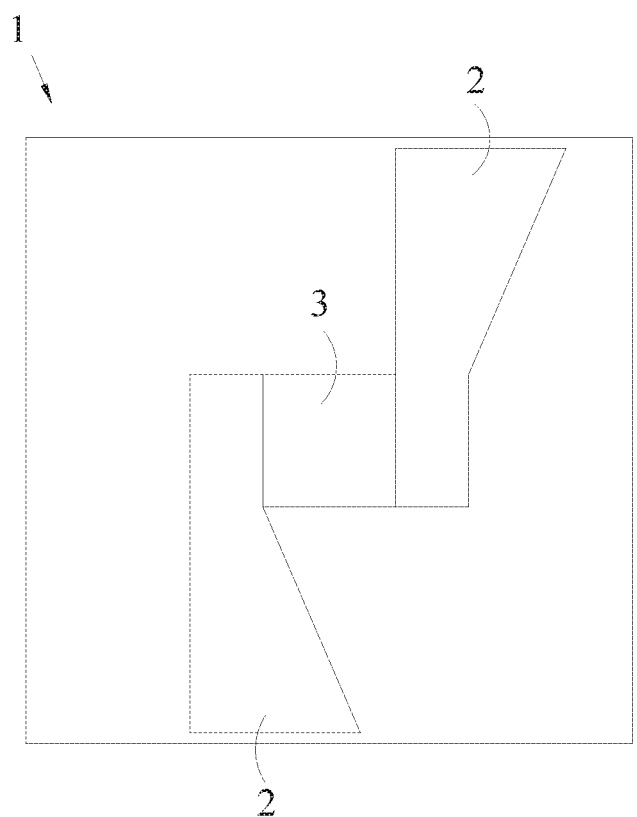
FIG. 1 is a schematic diagram of the biosensing chip according the embodiment of the present disclosure.

In the following description, for the purposes of explanation, many specific details are set forth in order to provide a thorough understanding of various exemplary embodiments or implementations of the present disclosure. However, it is obvious that various exemplary embodiments may be realized without these specific details or with one or more equivalent configurations. Furthermore, the various exemplary embodiments may be different, but need not be exclusive. For instance, the specific shapes, configurations, and characteristics of the exemplary embodiment may be implemented or realized in another exemplary embodiment without departing from the concept of the present disclosure.

Unless otherwise stated, the illustrated exemplary embodiments should be construed as providing exemplary features that provide different details of means in which the concept of the present disclosure may be realized in practice. Therefore, unless otherwise stated, the features, layers, films, panels, regions, and/or aspects of various embodiments may be additionally combined, separated, interchanged, and/or rearranged without departing from the concept of the present disclosure.

In addition, the size and relative sizes of elements may be exaggerated for clarity and/or descriptive purposes in the drawings. When the exemplary embodiments are realized differently, a specific processing order may be performed differently from the described order. For instance, two consecutively described processes may be substantially performed simultaneously or in a reverse order contrary to that as described. Likewise, the same numerals refer to the same components.

Unless otherwise defined, all terms (including technical and scientific terms) used in the present disclosure have the same meaning as those commonly understood by a person of ordinary skill in the art. For instance, the terms defined in commonly used dictionaries should be interpreted as having meanings consistent with their meanings in the related art, and should not be interpreted in idealized or overly formal meanings unless clearly defined herein.

Figure 2:
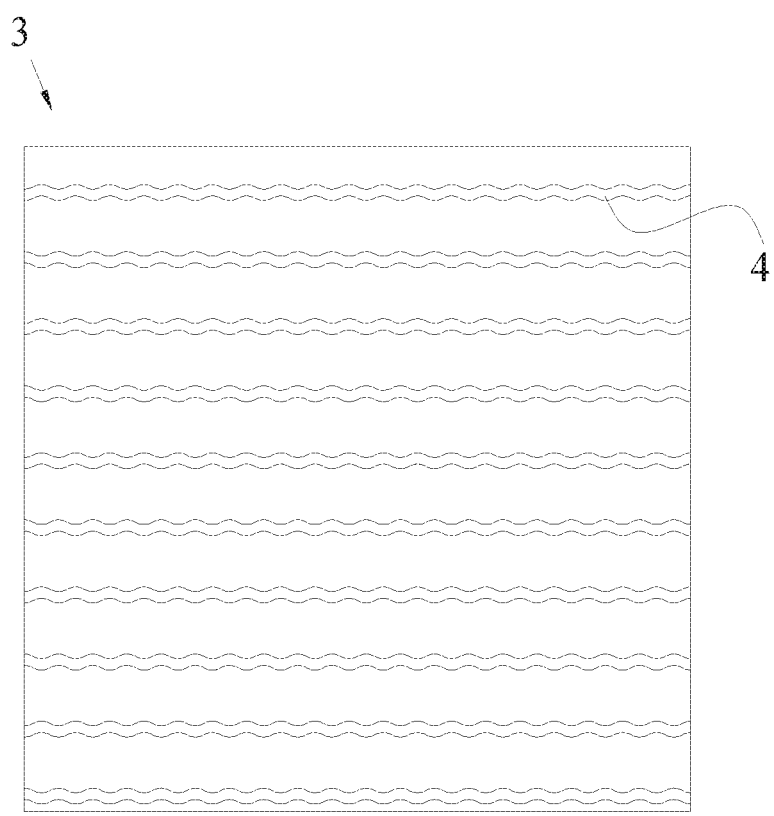
FIG. 2 is an enlarged diagram of the micro-electrodes of the biosensing chip according to the embodiment of the present disclosure.

FIG. 1 is a schematic diagram of the biosensing chip 1 according the embodiment of the present disclosure. FIG. 2 is an enlarged diagram of the electrode pattern 3 of the biosensing chip according to the embodiment of the present disclosure.

Figure 3:
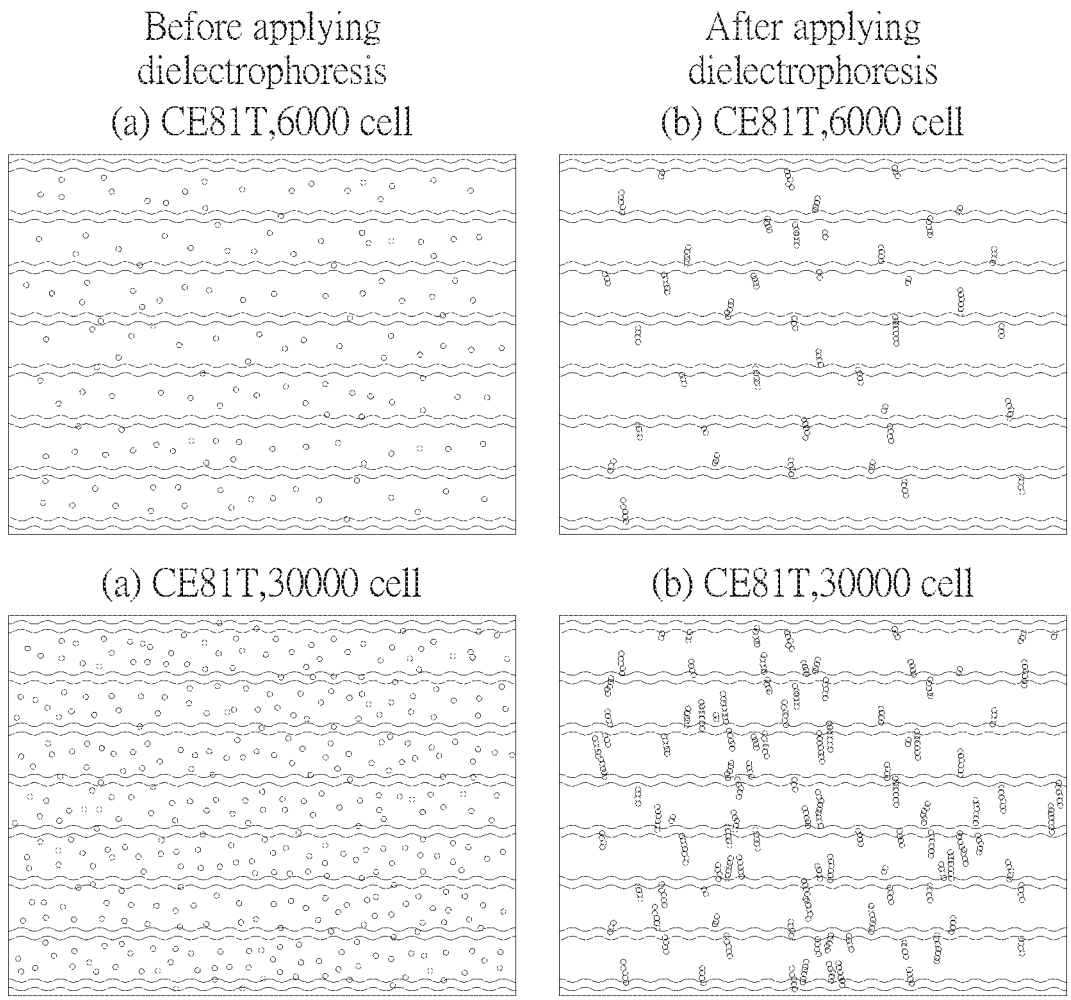
FIG. 3 is a photo of cells before and after being applied with dielectrophoresis using a biosensing chip under an optical microscope according to the embodiment of the present disclosure.

Referring to FIG. 1, the biosensing chip 1 of the embodiment of the present disclosure includes electrodes 2 and an electrode pattern 3. To measure an impedance value of quantitative cells concentrated between the electrodes, interdigitated sawtooth electrodes, in a shape of circular and straight lines with an electrode gap radius of 30 μm to 80 μm, preferably 40 μm to 60 μm, more preferably 50 μm, have been designed to perform cell manipulation and measurement, as shown in FIG. 3. The distance between the wavy or sawtooth micro-electrodes 4 included in the electrode pattern 3 is 60 μm to 160 μm, preferably 80 μm to 1200 μm, more preferably 100 μm. This is designed for the measurement of quantitative cells concentrated between the electrodes, for the assurance of the capability of generating enough dielectrophoretic force on viable cells when a high-frequency voltage is applied, and for a higher sensibility compared to normal micro-electrodes.

Monocrystalline silicon is used as a substrate for the chip of the present embodiment for the manufacturing process. In addition to the monocrystalline silicon material, materials with the photoelectric effect may also be used, namely a metal oxide (such as cuprous oxide and zinc oxide), an III-V compound semiconductor, and an II-VI compound semiconductor material. A monocrystalline silicon substrate has a higher photoelectric conversion efficiency, and a chip is manufactured using the standard yellow light lithography process. A pattern defined by the photomask is used for the process to make a required electrode pattern on the substrate. The process of the chip is divided into two steps: the Au/Cr electron beam evaporation and the electrode lithography process, and the procedure for the process is detailed as follows:

Au/Cr Electron Beam Evaporation

The process is mainly performed by bombarding the target material in a vacuum environment for physical vapor deposition. By Using the electron beam evaporation method, the kinetic energy of a high-energy electron beam being converted into the thermal energy which melts the target material, and the coating is performed by the saturated vapor pressure of the target material close to the melting point. The material to be vaporized is heated until vaporization and sublimation are reached and the gas is attached to the surface of the substrate placed nearby to form a thin film. Compared to the thermal resistance vapor deposition method in the past, this method may not only overcome the limitation on the target material, but also effectively reduce the pollution that may be caused during vapor deposition. In terms of an evaporation rate, the use of electron beam evaporation may also accurately control the rate by controlling the current, so that the rate may reach an evaporation rate of 1 nm per minute.

The Sample Holder above the electron beam evaporation system used in the present disclosure may be placed with up to six samples with a size like four-inch wafer, and up to four kinds of target materials may be placed in a single evaporation process. According to the needs of the experiment, a heating lamp may also be used to provide a high-temperature environment (to 250° C.).

Electrode Lithography Process a. Spin-coating:

An S1813 positive photoresist is adopted for the process. Firstly, the silicon substrate is cut into an appropriate size and the surface is cleaned with acetone, methanol, and DI water. A glass chip is placed in a photoresist coating machine, and an appropriate amount of the S1813 positive photoresist is dropped for coating. To make the photoresist evenly coated on the glass, the setting of the coating machine is divided into two phases. For the first phase, spin-coating is performed for 10 seconds at a rotation speed of 700 rpm. In this phase, the excess S1813 photoresist may be removed initially at a lower speed. For the second phase, the spin-coating is performed for 20 seconds at a rotation speed of 1700 rpm. In the second phase, the higher rotation speed may make the photoresist being evenly spin-coated on a substrate with a thickness of about 3 μm.

b. Soft-Bake:

After the completion of spin-coating, the photoresist is placed on a 90° C. heating plate for 4 minutes for soft-bake. The purpose of the step is to evaporate the organic solution in the photoresist by heating and avoid the sticking of the photoresist and the photomask during exposure. Also, the photoresist may be flatter and the adhesion between the photoresist and the substrate may be enhanced. If temperature and time for soft-bake are insufficient, too much organic solution may be left, resulting in a decrease in the graphic resolution. In contrast, the sensitivity of the photoresist to light may be reduced, resulting in lithography less likely to be developed.

c. Exposure:

Lithography may be divided into UV lithography, E-beam lithography, and X-ray lithography according to different light sources. The yellow light lithography process is used in the present disclosure because the light source is low-pressure and high-pressure mercury lamp or mercury-xenon arc lamp. In the ultraviolet wavelength range of 350 nm to 450 nm, these two light sources have two high-intensity emission spectrum lines, such as g-line (436 nm) and i-line (365 nm). The purpose of the exposure is mainly to allow the photoresist to have bonding or breaking, so the part exposed to the light has a great difference in the solubility of the developing solution, thus achieving the purpose of pattern transfer. Before the exposure, an illuminometer (Power Memter) has to be used to measure the exposure power (mW/cm$^2$) of the exposure machine to calculate the time required for the exposure.

The theoretical equation of exposure time is exemplified as follows:

Exposure dosage (mJ/cm$^2$)=exposure power (mW/cm$^2$)×exposure time (sec)

The soft-baked chip is then exposed to light. The photomask with an electrode pattern is covered on the S1813 photoresist which is coated on the silicon substrate for follow-up exposure.

d. Post-Exposure Bake:

During the exposure, part of the light not absorbed by the photoresist reaches the surface of the substrate through the photoresist. Since the reflected and incident light waves generate constructive and destructive interference to form a standing wave effect. This effect may make the photoresist receive uneven light intensity so that the side of the photoresist may be rippled, resulting in the line width of the photoresist to change and affecting the follow-up process. Therefore, the post-exposure bake is able to rearrange the exposed photoresist to reduce the occurrence of the abnormality caused by the standing wave effect. In this experimental process, the post-exposure bake is performed on the chip at 90° C. for 4 minutes.

e. Development:

In this embodiment, development is conducted with the special developing solution MP351 of S1813, and the preparation ratio is MP351:DI water=1:4 (v/v). The glass chip is placed in the mixed developing solution MP351 and shaken evenly for about 10 to 15 seconds. When the photoresist layer drops, the development is completed. If the photoresist does not drop, this action is repeated until the photoresist drops. Finally, cleaning is performed using DI water to complete a barrier layer required for follow-up etching.

f. Hard Bake:

Before the completion of the development process, hard bake has to be conducted. The chip is placed on a heating plate at 120° C. and baked for 10 minutes, the purpose of which is to further minimize the residual solvent content in the photoresist layer and enhance the adhesion of the photoresist layer to the surface. The bonding of the photoresist layer is also strengthened to enhance the acid resistance to benefit etching.

g. Etching:

Etching refers to the technique of acidic, corrosive, or abrasive substances on a glass surface. The current etching technology is mostly used in semiconductor processes and may be divided into dry etching and wet etching. The wet etching is used in this experiment. The chip is placed in a gold etching solution and soaked for 3 minutes until unnecessary gold films on the substrate are removed. If the gold films are not removed, the soaking time is increased until the gold films are removed. After the etching of the gold films, the gold chip is placed in the chromium etching solution. After 3 minutes of soaking, the chip is taken out and cleaned with DI water. Moreover, a microscope is used to observe whether the electrode pattern is complete. That is, the etching step is completed.

h. Photoresist Removal:

The residual photoresist on the surface of the glass is cleaned with acetone, methanol, and deionized water to complete the manufacturing of the chip.

It should be noted that the biosensing chip according to the embodiment of the present disclosure may be manufactured by any suitable method and process without being limited to the method as mentioned above.

The method for using the biosensing chip of the present disclosure is described in detail below according to the exemplary embodiment.

Experiment for Distinguishing Cancer Cells

Through the impedance measurement system and the micro-current meter, the present disclosure distinguishes four different cancer cells at different sites and the same sites from different human races with the use of the biosensing chip. The cancer cells respectively are OE21 esophageal cancer cells, CE81T/VGH esophageal cancer cells, A549 lung adenocarcinoma cells, and TSGH-8301 bladder cancer cells. In this experiment, the cells are cultured, counted, and replaced before measurement, wherein in terms of the impedance measurement, the interdigitated sawtooth microelectrodes using dielectrophoretic impedance measurement (DEPIM) may generate a positive dielectrophoretic force on the electrodes to generate high electric field areas to aggregate four cancer cells on the tip of the microelectrodes. Afterward, the measurement is performed with a sinusoidal function signal. In the measurement, it is expected that the cells may be aggregated by the dielectrophoretic force and a gap between the interdigitated electrodes may have a higher surface area to accommodate the cells. Moreover, the admittance value may be obtained after calculation for a follow-up analysis. In terms of the photocurrent measurement, a bias voltage is applied to the chip using a micro-current meter through a probe. Photoexcited carriers are generated through an element absorbing light. The concentration of GSH and GSSG has a catalytic effect on the separation of electrons and holes to further detect the relationship between the degree of cancer lesions and the photocurrent.

The Preparation of a Cancer Cell Medium

In this experiment, four different types of cancer cells are used, which respectively are CE81T esophageal cancer cells, OE21 esophageal cancer cells, A549 lung adenocarcinoma cells, and TSGH-8301 bladder cancer cells. The medium should be prepared according to the requirement for the cells. The medium required for TSGH8301 cells is RPMI-160. The medium required for CE81T, CE81T-4, A549 cells is DMEM. When in preparation, RPMI-160 has to be added with 2.0 g/L sodium bicarbonate (NaHCO$_3$) to balance pH. Then, an environment suitable for the cells to grow is adjusted using hydrochloric acid (HCl) or sodium hydroxide (NaOH), wherein the pH value is usually 7.1 to 7.3. Further, filtering is conducted with a filter film (0.22 μm). After sterilization, the glass jar is sealed and put into a refrigerator. Finally, before use, 1% of (v/v) antibiotics (Antibiotic-Antimycotic, Gibco, Grand Island, N.Y., USA) and 10% of (v/v) fetal bovine serum (Heat-inactivated fetal bovine serum, FBS, Gibco, Grand Island, N.Y., USA), which respectively inhibit the growth of bacteria or mold and provide necessary nutrients for cells to grow, are added in the medium. When in preparation, DMEM has to be added with 3.7 g/L sodium bicarbonate (NaHCO$_3$) to balance pH. Then, an environment suitable for the cells to grow is adjusted using hydrochloric acid (HCl) or sodium hydroxide (NaOH), wherein the pH value is usually 7.1 to 7.3. Further, filtering is conducted with a filter film (0.22 μm). After sterilization, the glass jar is sealed and put into a refrigerator. Finally, before use, 1% of (v/v) non-essential amino acids (Non-Essential Amino Acids, Gibco, Grand Island, N.Y., USA), 1% of (v/v) antibiotics (Antibiotic-Antimycotic, Gibco, Grand Island, N.Y., USA), and 10% of (v/v) fetal bovine serum (Heat-inactivated fetal bovine serum, FBS, Gibco, Grand Island, N.Y., USA), which respectively inhibit the growth of bacteria or mold and provide necessary nutrients for cells to grow, are added in the medium.

Cell Solution/Sample Preparation

In the dielectrophoresis experiment, the electrical difference between the cells and the surrounding solution is the key to the overall experiment, and also affects the CM factor of the dielectrophoresis phenomenon. Therefore, the phenomenon of dielectrophoresis is unlikely to occur. Therefore, it is necessary to select an appropriate solution to conduct the dielectrophoresis experiment. In addition, in consideration of biological cells, when the cells are soaked in a solution with high osmotic pressure (pure water), the cells may burst. If the solution is under low osmotic pressure (saline), the cells may shrink. Neither of the above may perform viable cell experiments. In the experiment, if the solution is of high electric conductivity, such as medium, dielectrophoresis may not be generated. As to the PBS solution, Joule heat and bubbles may occur, leading to the damage to the electrodes and the death of cells. Therefore, in the experiment, an equal tensor of the sucrose solution of 8.62% with an electric conductivity of 17.6 μS/cm is used as the experimental solution for the experiment to keep the cells active during the experiment. Before the experiment, the cell solution is replaced using centrifugation, and the cells are collected at the bottom of the centrifuge tube with a rotation speed of 550 rpm/5 minutes. After drawing the upper layer solution, an equal tensor of sucrose solution is added. After this step is repeated ten times, the solution replacement is completed. Then, dielectrophoresis and measurement experiments may only be conducted after the cells are counted.

The Constructing of the Impedance Measurement System

The present experiment uses Microtest 6630 Precision Impedance Analyzer. An AC frequency with 1 Vp-p voltage is used for measurement together with a signal generator (function generator, Agilent 33220A) because the signal generator may provide excitation signals with a wide range of amplitudes and frequencies. A vertical type microscope (OLYMPUS, BX43) with a CCD camera lens (DP71, Olympus, Tokyo, Japan) is connected to a computer for observation and recording of the variation in cell samples.

Experiment Procedure of the Impedance Measurement

To begin with, manufactured chips are measured for impedance first. Since some factors generated in the process, such as electrode peeling and breaking, may cause impedance values to be too large, chips with overly large impedance values are scrapped after confirmation. Otherwise, a probe is fixed using a micro-positioning probe base for making contact with the electrode 2 on the biosensing chip 1. Fixing the probe by the micro-positioning probe base may allow the probe to be more stable and unlikely to shake. A admittance value of sucrose is measured at the beginning of the experiment. The number of cell samples is counted using a counting board and then dropped on an electrode pattern 3 of the biosensing chip 1. Since the dropped cells may disperse in the solution, it is necessary to wait for 5 minutes for the cells to settle to the bottom of the chip. A voltage at 1 MHz and 10 Vp-p is applied for 5 minutes to generate dielectrophoresis to aggregate cells. The measurement is then performed after the cells are formed into a string of pearls between the micro-electrodes 4. A voltage at 500 kHz and 1 Vp-p is used for the measurement, and ideal measurement data may be obtained after the signal is more stable. The measured signals are collected, calculated, and transmitted to the computer through the data port. Then, Origin software is used for data processing to obtain the admittance value of the cell samples.

The Constructing of the Photoelectric Response System

The present experiment uses a micro-current meter (AMETRIX Instruments Model 101) as the main measurement for a photocurrent measuring system. The resolution and precision provided by the micro-current meter are superior to those provided by a more expensive conventional instrument, and the micro-current meter also provides more silent and stable measurement and greatly shortens the time for measurement. Through the micro-positioning probe base (Micropositioner EB-700), the photocurrent response measuring system fixes the probe pressure and probe position. A bias voltage is applied to the chip by the micro-current meter via the probe, and a light source excites carriers of samples for separation. The probe is further connected to measure the photocurrent response. The aforementioned may require the setting of the values through software.

Experimental Steps of the Photocurrent Response

To begin with, the manufactured biosensing chip 1 is cleaned first. The biosensing chip 1 is blow-dried with nitrogen after cleaning with DI water. After the cleaning, a probe is fixed using a micro-positioning probe base for making contact with the biosensing chip 1. Fixing the probe by the micro-positioning probe base may allow the probe to be more stable and unlikely to shake. The micro-current meter is controlled through the software (Pluse Scan V1.1) written by LabVIEW RTE2013. A bias voltage at 1 v is applied through the micro-current meter, and the samples are excited using an indoor light source. The indoor light source is likely to be obtained and the distance between the light source and the chip may be fixed. The experiment has to be conducted in a dark room because the experiment conducted in a dark room may prevent interference from an external light source which would make the signal unstable. The number of cell samples is counted using a counting board and then dropped on an electrode pattern 3 of the biosensing chip 1. In the beginning, the biosensing chip 1 is stabilized for about 30 seconds to 1 minute, preferably 30 seconds, to obtain the ideal data. Afterward, the photocurrent response of the chip is measured with the regularity of turning on the light for 10 seconds to 30 seconds and turning off the light for 10 seconds to 70 seconds, preferably a cycle of turning on the light for 10 seconds and turning off the light for 10 seconds. The aforementioned may require collecting the value of the photocurrent response through the software. The measured signals are collected, calculated, and transmitted to the computer through the data port. Then, Origin software is used for data processing to obtain the photocurrent response of the cell samples.

Results

Dielectrophoresis for the Aggregation of Cells.

FIG. 3 is an optical microscope image before and after an AC voltage at 10 Vp-p is applied to the biosensing chip. (a) is 6000 CE81T cells before applying dielectrophoresis. (b) is 6000 CE81T cells after applying dielectrophoresis. (c) is 30000 CE81T cells before applying dielectrophoresis. (c) is 30000 CE81T cells after applying dielectrophoresis. In the experiment, the Oriental esophageal cancer cell CE81T is used as an example. A sinusoidal wave with 1 MHz and 10 Vp-p is applied to the electrodes to perform dielectrophoresis (DEP) aggregation for 10 minutes. The aggregation range of numbers of cells ranges from 3000 to 30000 cells. At the moment, the cells exhibit a positive dielectrophoretic force. FIG. 3 (*a*) and FIG. 3 (*c*) respectively are optical microscope images of 6000 and 30000 esophageal cancer cells before applying dielectrophoresis. FIG. 3 (*b*) and FIG.

3 (d) respectively are optical microscope images of 6000 and 30000 esophageal cancer cells after applying dielectrophoresis. As shown in FIG. 3, after applying dielectrophoresis, the cells are aggregated around the tip of the micro-electrodes 4 in the shape of a string of pearls.

Results of the Dielectrophoretic Impedance Measurement

Figure 4:
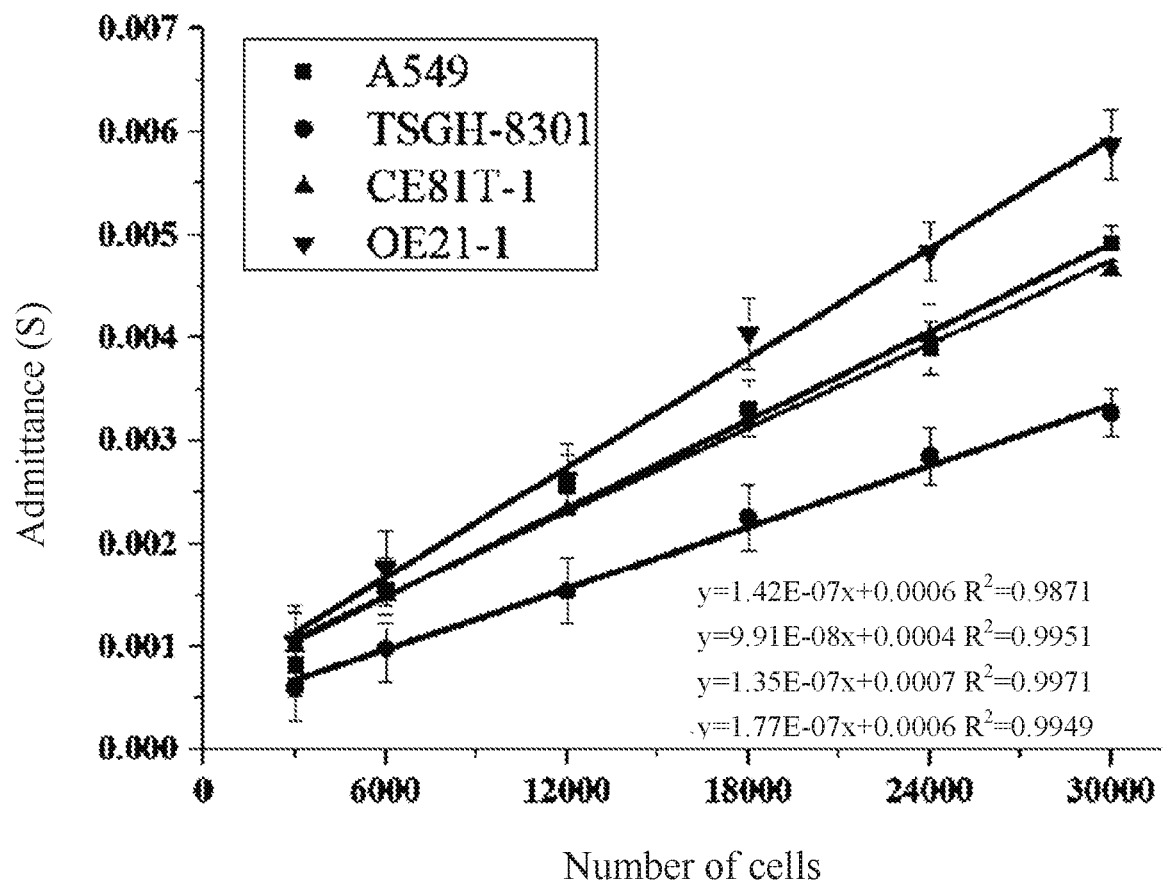
FIG. 4 is a variation in the admittance value of four types of cancer cells according to the embodiment of the present disclosure.

In the equation of the equivalent circuit module, the impedance and admittance are known to have a reciprocal relation. When measuring the biosensing chip 1 before the experiment, no cells are injected above the electrode pattern 3 of the biosensing chip 1, and the impedance of the sucrose solution is simply measured. The admittance value of sucrose is obtained from the calculation of the impedance value at the moment. Then, in various tests of different numbers of cells, the admittance value and the admittance value of the reference sample are obtained to calculate the correct variation in the admittance value. FIG. 4 is a relational chart of the variation in the admittance value of the four cancer cells, which respectively are OE21-1 Caucasian esophageal cancer cells, CE81T-1 esophageal cancer cells, A549 lung adenocarcinoma cells, and TSGH-8301 bladder cancer cells, under different numbers of cells, showing the variation in the admittance value after the biosensing chip 1 is injected with the cells. From FIG. 4, it may be seen that a linear relationship exists between the variation in the admittance value and the numbers of cells, and linear regression is also over 90%. The variation in the relational chart between the admittance value and the numbers of cells shows different slopes for cancer cells in different sites. Cancer cells in different sites may be identified by the difference in slope.

Results of Photoelectrochemical Response Measurement

Figure 5:
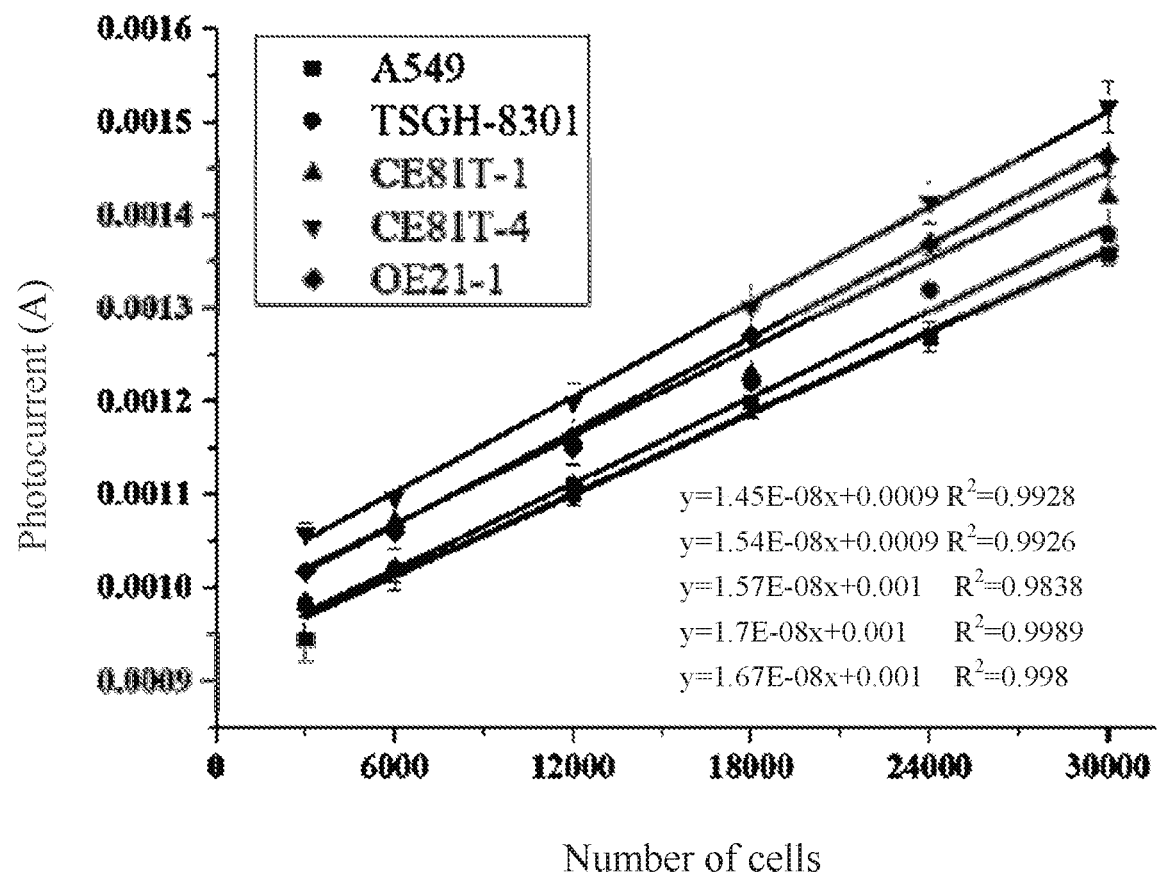
FIG. 5 is a result of the photocurrent response measurement of four types of cancer cells under different numbers of cells according to the embodiment of the present disclosure.
Figure 6:
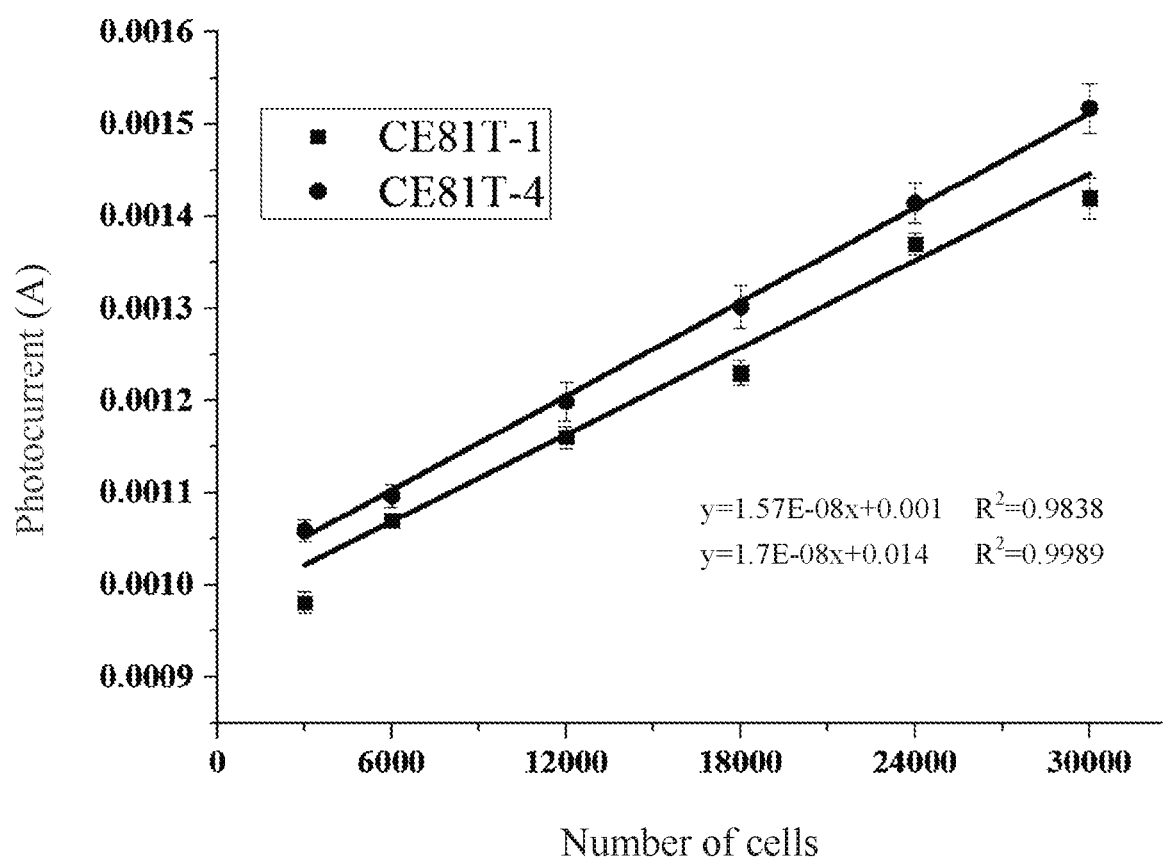
FIG. 6 is a result of the photocurrent measurement of CE81T esophageal cancer cells under different numbers of cells.

The data of photocurrent response initially obtained in the present experiment is calculated so that the photocurrent values before the light is turned on are all the same. Furthermore, the data of the photocurrent is obtained at a fixed time point after the light is turned on for obtaining correct photocurrent values. FIG. 5 shows the results of the photocurrent response measurement of four types of cancer cells under different numbers of cells, wherein CE81T-1 and CE81T-4 are the first-stage lesion and the fourth-stage lesion in Oriental esophageal cancer cells, and OE21-1 is the first stage of Caucasian esophageal cancer. The cancer cells in different sites and the degree of cancer lesions measured by a micro-current meter and the photocurrent response curve obtained by the measurement under different numbers of cancer cells are shown in FIG. 5. It may be seen that a linear relationship exists between the photocurrent response and the numbers of cancer cells. From the figure, it is known that the photocurrent response of cancer cells with different degrees of cancer lesions has a large difference with the slope of the numbers of cells. FIG. 6 is the result of the photocurrent measurement of CE81T esophageal cancer cells under different numbers of cells, wherein CE81T-1 is the first-stage cancer lesion and CE81T-4 is the fourth-stage cancer lesion. From the measurement result of FIG. 6, cancer cells with different degrees of cancer lesions identified using the difference in slope may be inferred.

Figure 7:
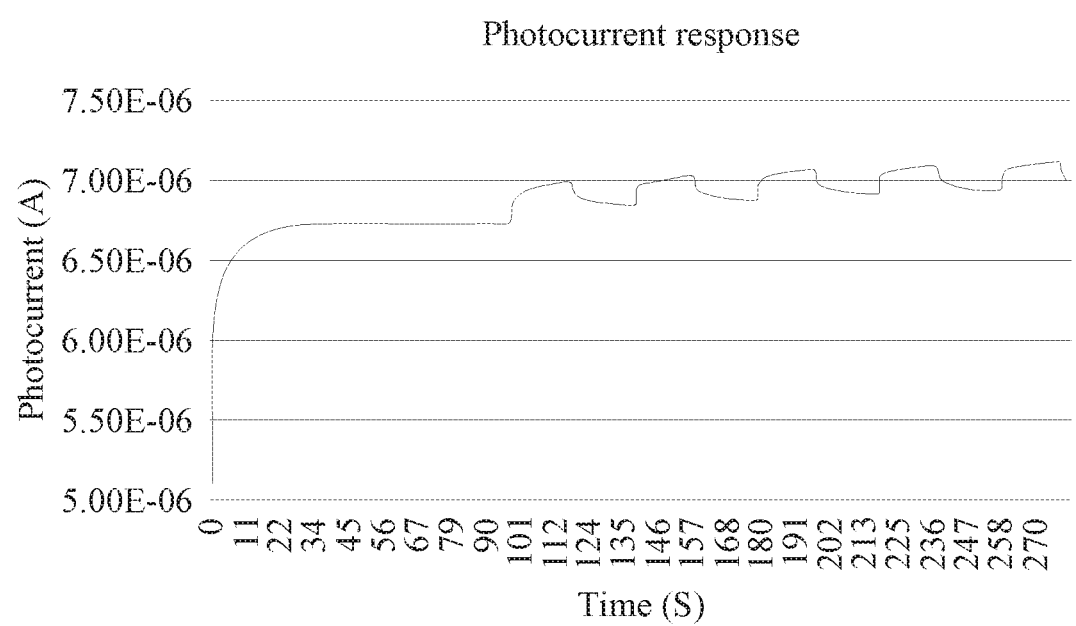
FIG. 7 is an impedance measurement value of using the biosensing chip according to the embodiment of the present disclosure to simultaneously measure the admittance value and the photocurrent.
Figure 8:
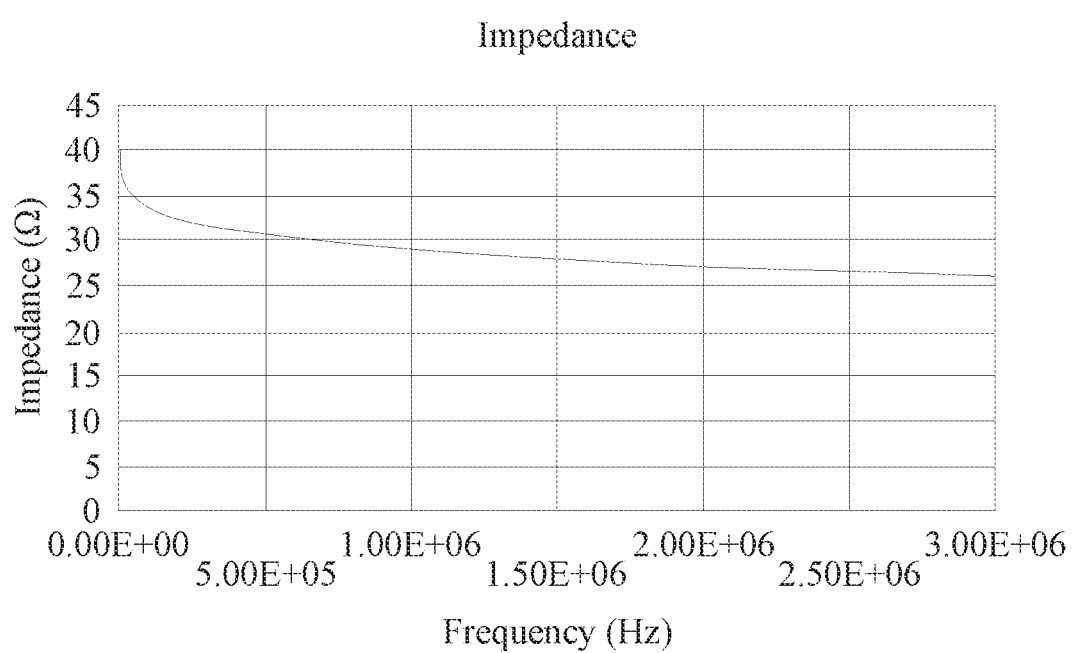
FIG. 8 is a photocurrent measurement value of using the biosensing chip according to the embodiment of the present disclosure to simultaneously measure the admittance value and the photocurrent.

Then, refer to FIG. 7 and FIG. 8. FIG. 7 is an impedance measurement value of using the biosensing chip according to the embodiment of the present disclosure to simultaneously measure the admittance value and the photocurrent. FIG. 8 is a photocurrent measurement value of using the biosensing chip according to the embodiment of the present disclosure to simultaneously measure the admittance value and the photocurrent. According to the biosensing chip of the embodiment of the present disclosure, the cell admittance value and the photoelectric response may be measured simultaneously.

Two ends of the admittance measurement probe and two ends of the measurement photocurrent probe are respectively connected to the corresponding electrodes 2 in FIG. 1. Then, an impedance measuring instrument and a photocurrent measuring instrument are controlled for simultaneous measurement using self-made inspection software. The photoelectric response and cell admittance value may be measured simultaneously using the circuit-designing framework and self-made measurement software. The measurement results as shown in FIG. 7 and FIG. 8 are the measurement values of cell photoelectric response and cell admittance value.

Finally, the biosensing chip provided by the present disclosure and the proposed method successfully distinguishes OE21 esophageal cancer cells, CE81T/VGH esophageal cancer cells, A549 lung adenocarcinoma cells, TSGH-8301 bladder cancer cells using the difference in slope and has the function of detecting the same site with different degrees of cancer lesions. The biosensing chip of the embodiment of the present disclosure only requires a small amount of time to detect and analyze cancer cells without complicated and expensive equipment. Moreover, in the results of impedance measurement and photocurrent response measurement, the cell number and admittance value and the cell number and photocurrent value basically have a linear relationship, and these cancer cells may be distinguished by the difference in slope.

The above description is merely illustrative rather than restrictive. Any equivalent modifications or alterations without departing from the spirit and scope of the present disclosure are intended to be included in the following claims.

What is claimed is:

1. A biosensing chip, comprising:
   a substrate comprising a photoelectric conversion material; and
   an electrode disposed on the substrate and comprising two contact portions and an electrode pattern;
   wherein the photoelectric conversion material is a monocrystalline silicon material, a metal oxide, an III-V compound semiconductor, or an II-VI compound semiconductor material, and
   wherein the electrode pattern comprises a plurality of micro-electrodes spaced apart from each other by a gap formed of a plurality of circular shapes partially overlapping each other in a straight line, and the plurality of circular shapes forming the gap having a radius of about 30 µm to 80 µm.

2. The biosensing chip according to claim 1, wherein the plurality of micro-electrodes are spaced apart from each other by about 60 µm to 160 µm.

3. The biosensing chip according to claim 1, wherein the electrode is made of gold-chromium alloy, graphene, or graphene oxide.

4. A method for distinguishing a lesion site of cancer cells, comprising:
   applying a cell suspension liquid comprising a test cell after being quantified to an electrode pattern of a biosensing chip according to claim 1;
   applying an electric signal to two contact portions of the biosensing chip by a signal generator; and
   connecting a sensor to the two contact portions of the biosensing chip to measure an admittance value of the test cell.

5. The method according to claim 4, wherein the electric signal is a voltage at 1 MHz and 10 Vp-p lasting for about 5 minutes.

6. The method according to claim 4, wherein in a step of measuring the admittance value of the test cell, the sensor measures with a voltage at 500 kHz and 1 Vp-p.

7. A method for distinguishing a degree of cancer lesions, comprising:

applying a cell suspension liquid after being quantified to an electrode pattern of a biosensing chip according to claim 1;

connecting a sensor to the two contact portions of the biosensing chip to sense signals;

waiting for a first predetermined time to stabilize the biosensing chip in a dark room;

turning on a light for a second predetermined time, then turning off the light and lasting for a third predetermined time, and collecting values of a photocurrent response by the sensor.

8. The method according to claim 7, wherein the first predetermined time is about 30 seconds to 1 minute, the second predetermined time is about 10 seconds to 30 seconds, and the third predetermined time is about 10 seconds to 70 seconds.

* * * * *